United States Patent
Motamedi et al.

(10) Patent No.: US 6,725,073 B1
(45) Date of Patent: Apr. 20, 2004

(54) METHODS FOR NONINVASIVE ANALYTE SENSING

(75) Inventors: Massoud Motamedi, Houston, TX (US); Rinat O. Esenaliev, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/197,655

(22) Filed: Jul. 17, 2002

Related U.S. Application Data

(63) Continuation of application No. 09/640,891, filed on Aug. 17, 2000, now abandoned.
(60) Provisional application No. 60/149,538, filed on Aug. 17, 1999.

(51) Int. Cl.$^7$ .................................................. A61B 5/00
(52) U.S. Cl. ......................... 600/316; 600/322; 600/365
(58) Field of Search ................................ 600/309–310, 600/365, 316, 322

(56) References Cited

U.S. PATENT DOCUMENTS

| | | | | |
|---|---|---|---|---|
| 5,710,630 A | * | 1/1998 | Essenpreis et al. | 600/316 |
| 6,485,413 B1 | * | 11/2002 | Boppart et al. | 600/160 |

FOREIGN PATENT DOCUMENTS

| | | |
|---|---|---|
| EP | 807812 | 11/1997 |
| WO | WO 92/19930 | 11/1992 |

OTHER PUBLICATIONS

King et al., "Multrispectral polarimetric glucose detection using a single pockels cell," *Optical Engineering*, 33:2746–2753, 1994.

Robinson et al., "Noninvasive glucose monitoring in diabetic patients: a preliminary evaluation," *Clin. Chem.*, 38:1618–1622, 1992.

Bantle and Thomas, "Glucose measurement in patients with diabetes mellitus with dermal interstatial fluid," *J. Lab. Clin. Med.*, 130:436–441, 1997.

*Absorption and scattering of light by small particles*, eds. Bohren and Huffman, Wiley and Sons Publishing.

Boppart et al., "Noninvasive assessment of the developing Xenopus cardiovascular system using optical coherence tomography,", *Proc. Nat'l Acad. Sci. USA*; 94:4256–4261, 1997.

Brezinski et al., "Assessing atherosclerotic plaque morphology: comparison of optical coherence tomography and high frequency intravascular ultrasound," *Heart*, 77(5):397–403, 1997.

Brezinski et al., "Optical biopsy with optical coherence tomography: feasibility for surgical diagnostics," *Journal of Surgical Research*, 71:32–40; 1997.

Bruulseman et al., "Correlation between blood glucose concentration in diabetes and noninvasively measured tissue optical scattering coefficient," *Optic Letters*, 22(3):190–192, 1997.

(List continued on next page.)

*Primary Examiner*—Eric F. Winakur
*Assistant Examiner*—Matthew Kremer
(74) *Attorney, Agent, or Firm*—Fulbright & Jaworski L.L.P.

(57) ABSTRACT

Methods for measuring analyte concentration within a tissue using optical coherence tomography (OCT). Radiation is generated, and a first portion of the radiation is directed to the tissue to generate backscattered radiation. A second portion of the radiation is directed to a reflector to generate reference radiation. The backscattered radiation and the reference radiation is detected to produce an interference signal. The analyte concentration is calculated using the interference signal.

44 Claims, 8 Drawing Sheets

OTHER PUBLICATIONS

Chen et al., "Noninvasive imaging of in vivo blood flow velocity using optical Doppler tomography," *Optic Letters*, 22(14):1119–1121, 1997.

Colston et al., "Optical coherence tomography for diagnosing periodontal disease," *SPIE*, 2973:216–220, 1997.

Colston et al., "Imaging of hard– and soft–tissue structure in the oral cavity by optical coherence tomography," *Applied Optics*, 37(16):3582–3585, 1998.

Coté; Noninvasive optical glucose sensing—an overview, *Journal of Clinical Engineering*, 22(4):253–259, 1997.

Coté et al., "Noninvasive optical polarimetric glucose sensing using a true phase measurement technique," *IEEE Transactions on Biomedical Engineering*, 39(7):752–756, 1992.

Fercher et al., "In vivo optical coherence tomography," *American Journal of Ophthalmology*, 116(1):113–114, 1993.

Fujii et al., "Evaluation of Yucatan micropig skin for use as an in vitro model for skin permeation study," *Biol. Pharm. Bull.*, 20(3):249–254, 1997.

Goetz et al., "Application of a multivariate technique to Raman spectra for quantification of body chemicals," *IEEE Transactions on Biomedical Engineering*, 42(7), 1995.

Tuchin et al., "Light propagation in tissues with controlled optical properties," *SPIE*, 2925:118–142, 1994.

Van de Hulst, *Light Scattering by small particles*; Dover Publications, Inc., New York©, 1981.

Izatt et al., "In vivo bidirectional color Doppler flow imaging of picoliter blood volumes using optical coherence tomography," *Optics Letters*, 22(18):1439–1441, 1997.

Kohl et al., "The influence of glucose concentration upon the transport of light in tissue–simulating phantoms," *Phys. Med. Biol.*, 40:1267–1287, 1995.

Wicksted et al., "Monitoring of aqueous humor metabolites using Ramen spectroscopy," *SPIE*, 2135:264–274, 1994.

Larin and Oraevsky; "Optoacoustical signal profiles for monitoring glucose concentration in turbid media," Whitepaper, 1997.

Kurihara–Bergstrom et al. "Characterization of the Yucatan miniature pig skin and small intestine for pharmaceutical applications," *Laboratory Animal Science*, 36(4):396–399, 1986.

Maier et al., "Possible correlation between blood glucose concentration and the reduced scattered coefficient of tissues in the near infrared," *Optics Letters*, 19(24):2062–2064, 1994.

Pan et al., "Near–infrared spectroscopic measurement of physiological glucose levels in variable matrices of protein and triglycerides," *Analytical Chemistry*, 68(7):1124–1135, 1996.

Roper et al., "In vivo detection of experimentally induced cortical dysgenesis in the adult rat neocortex using optical coherence tomography," *Journal of Neuroscience Methods*, 80:91–98, 1998.

Sergeev et al., "In vivo optical coherence tomography of human skin microstructure," *SPIE*, 2328:144–150, 1994.

Sergeev et al., "In vivo endoscopic OCT imaging of pre-cancer and cancer states of human mucosa," *Optics Express*, 1(13):432–440, 1997.

Service et al., "Dermal interstitial glucose as an indicator of ambient glycemia," *Diabetes Care*, 20(9):1426–1429, 1997.

\* cited by examiner

METHODS FOR NONINVASIVE ANALYTE SENSING

This is a continuation of application Ser. No. 09/640,891, filed Aug. 17, 2000 now abandoned, which claims priority to provisional patent application Ser. No. 60/149,538 filed Aug. 17, 1999, entitled "Non-Invasive Glucose Sensing With a Novel Optical Technique." The entire text of this provisional patent application is specifically incorporated by reference herein without disclaimer.

BACKGROUND OF THE INVENTION

1. Field of the Invention

This invention relates to analyte level detection and monitoring in tissue. More particularly, this invention relates to methods for noninvasively detecting and monitoring the analyte concentration in tissue, body fluid such as blood, and implants using optical coherence tomography. The analyte concentration may include glucose concentration.

2. Description of Related Art

Approximately 14 million people in the United States, and more than 120 million people all over the world suffer from diabetes mellitus (commonly referred to as "diabetes" or "Willis' disease"), a chronic, systemic, metabolic disease that is the most common disorder of the endocrine system. The disease is brought on by disorders in blood levels of insulin, a pancreatic hormone that helps convert glucose, or blood sugar, into energy. Insulin is necessary for glucose to go from the blood to the inside of the cells, and unless the glucose gets into the cells, the body cannot use it. The excess glucose remains in the blood and is then removed by the kidneys.

Type 1 diabetes—sometimes called insulin-dependent diabetes mellitus (IDDM), or juvenile-onset diabetes—results from a shortage of insulin. With IDDM, the pancreas makes little or no insulin because the insulin-producing beta cells have been destroyed. IDDM usually appears suddenly and most commonly in younger people under age 30. Type 2 diabetes—also known as noninsulin-dependent diabetes mellitus (NIDDM), or adult-onset or stable diabetes—results from the body's inability to process insulin effectively. With NIDDM, the pancreas makes some insulin, and sometimes too much. However, the insulin is not effective because of its resistance by muscle cells. About 90 to 95 percent of all people with diabetes have Type 2 diabetes.

The complications of diabetes can demand as much attention as the disease itself. Most importantly, diabetes sufferers must monitor their blood sugar levels everyday to prevent an attack of hypoglycemia, in which available levels of blood sugar are too low to fulfill the body's energy needs. Hypoglycemia can easily be remedied, however, once its symptoms, such as weakness, dizziness, tingling in the hands and feet, and rapid heartbeat, are recognized. Diabetes may even result in a coma and causes about 60,000 deaths in the United States every year.

Long-term complications from diabetes can damage the eyes, nervous system, kidneys, and cardiovascular and circulatory systems, as well as hinder the body's overall resistance to infections. Cuts and sores heal more slowly for people with diabetes, who are also prone to gum problems, urinary tract infections, and mouth infections such as thrush, caused by an overgrowth of yeast organisms.

The proper treatment of diabetes includes maintenance of blood glucose at normal levels. Presently, the method by which diabetic patients control their blood glucose levels involves a finger puncture several times a day to obtain a droplet of blood for further chemical analysis. This inconvenient, invasive procedure limits the frequency of monitoring and, therefore, may give inadequate control of the long-term complications of the disease. The removal of this daily constraint would considerably improve the quality of life for diabetic patients, facilitate their compliance for glucose monitoring, and reduce complications and mortality caused by the disease. Thus, a noninvasive, quantitative method for monitoring blood glucose levels would be of great importance and would offer many people an improved way of life.

There have been significant efforts by many companies and scientific groups to monitor blood glucose concentration noninvasively using various, specific optical approaches: polarimetry, Raman spectroscopy, near infrared (NIR) absorption spectroscopy, and NIR scattering. Although each of these techniques has demonstrated at least a degree of utility in detecting glucose levels, shortcomings remain. In particular, each known method has unfortunate, inherent limitations: (1) low sensitivity (signal-to-noise ratio) for the glucose concentrations at clinically-relevant levels, and (2) insufficient specificity of glucose detection that requires development of complex algorithms for analysis of multi-component systems. In other words, the methods currently known (1) cannot provide adequate sensitivity to reliably and accurately monitor glucose levels typical in clinical situations and (2) cannot detect glucose reliably and accurately without resort to complicated analytical schemes that often rely upon several components, and which may add extra expense and undue complexity to the glucose-monitoring process. Thus, although current techniques may have demonstrated limited success in monitoring glucose levels, room for significant improvement remains. In particular, reducing or eliminating the limitations of the existing techniques would be very beneficial. More particularly, providing methods for detecting glucose levels within tissue in an accurate, reliable, and relatively simple manner would be advantageous.

Problems enumerated above are not intended to be exhaustive but rather are among many that tend to impair the effectiveness of previously known glucose-detection techniques. Other noteworthy problems may also exist; however, those presented above are sufficient to demonstrate that prior techniques appearing in the art have not been altogether satisfactory.

SUMMARY OF THE INVENTION

The present invention provides an optical coherent tomography (OCT) apparatus including a radiation source, a probe arm for directing a portion of the radiation into a tissue, body fluid such as blood, or an implant in an animal including a human, a collector for collecting reflected or back scattered light from the tissue, an interferometer having a first input for receiving the reflected or back scattered light and a second input for receiving source radiation from a reference arm and a detector for measuring the interference signal of the reflected light and correlating the signal to a glucose concentration.

The present invention also relates to a method for measuring blood glucose levels including directing a portion of radiation from a radiation source onto a tissue site of an animal including an human, collecting a reflected or back-scattered light from the tissue, feeding the reflected light and a second portion of radiation from the radiation source into an interferometer, measuring an interference signal and the signal to a glucose concentration.

The present invention also provides as method implemented on a computer for analyzing interferometer data and correlating the data to a glucose concentration.

In one respect, the invention is a method for measuring glucose concentration within a tissue. Radiation is generated. A first portion of the radiation is directed to the tissue to generate backscattered radiation. A second portion of the radiation is directed to a reflector to generate reference radiation. The backscattered radiation and the reference radiation is detected to produce an interference signal. The glucose concentration is calculated using the interference signal.

In other respects, the generating radiation may include generating low-coherence radiation. The generating low-coherence radiation may include generating low-coherence radiation using a super-luminescent diode. The generating radiation may include generating radiation from a plurality of sources. Two or more of the sources may be used to emit radiation having different wavelengths. A wavelength of the backscattered radiation may be substantially equal to a wavelength of the reference radiation. The radiation may have a first polarization and the backscattered radiation may have a second polarization, the second polarization being different from the first polarization. The tissue may include skin. The tissue may include a blood vessel. The tissue may include sclera. The tissue may include lip. The tissue may include tongue. The tissue may include oral tissue. The tissue may include ear. The backscattered radiation may emanate from a tissue depth of between about 150 microns and about 500 microns. The backscattered radiation may emanate from a tissue depth of between about 150 microns and about 400 microns. The backscattered radiation may emanate from a tissue depth of between about 150 microns and about 200 microns. The directing a first portion of the radiation may include scanning the first portion of the radiation across a specified portion of the tissue. The calculating may include determining the glucose concentration using a slope of the interference signal. The calculating may include determining a glucose-induced change in an optical property of the tissue. The optical property may include scattering, anisotropic factors, absorption, or index of refraction. The calculating may include determining a glucose-induced change in morphology of the tissue. The morphology may include thickness or shape.

In another respect, the invention is a method for measuring analyte concentration within a tissue. Radiation is generated. A first portion of the radiation is directed to the tissue to generate backscattered radiation. A second portion of the radiation is directed to a reflector to generate reference radiation. The backscattered radiation and the reference radiation are detected to produce an interference signal. The analyte concentration is calculated using the interference signal.

In other respects, the analyte concentration may include glucose concentration.

In another respect, the invention is a method for measuring glucose concentration within a tissue. Radiation backscattered from the tissue and reference radiation are detected to generate an optical coherence tomography (OCT) signal. The glucose concentration within the tissue is determined using a slope of the OCT signal.

In other respects, a wavelength of the radiation backscattered from the tissue may be substantially equal to a wavelength of the reference radiation. Using the slope may include correlating the slope with an optical property of the tissue. Using the slope may include correlating the slope with a morphological property of the tissue. Using the slope may include correlating a percentage change in the slope with a change in glucose concentration.

In another respect, the invention is method for measuring analyte concentration within a tissue. A probe is implanted within the tissue, the probe being configured to alter an optical coherence tomography (OCT) signal of the tissue. An OCT signal of the tissue is generated, the OCT signal being altered by the probe. A change in slope of the OCT signal is correlated with the analyte concentration within the tissue.

In other respects, the probe may be configured to increase a sensitivity of the OCT signal.

In another respect, the invention is a computer readable media containing program instructions for measuring glucose concentration within a tissue. The computer readable media includes instructions for storing an optical coherence tomography (OCT) signal in memory and instructions for determining the glucose concentration within the tissue using the signal.

In other respects, the media may be stored within an OCT apparatus. The media may be stored within a personal computer. The media may be stored within a hand-held computing device. The instructions for determining the glucose concentration may include instructions for determining a slope of the OCT signal and for determining the glucose concentration using the slope. The instructions for determining the glucose concentration may include instructions for correlating a change in the slope with an optical or morphological change in the tissue.

Other features and advantages of the present invention will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
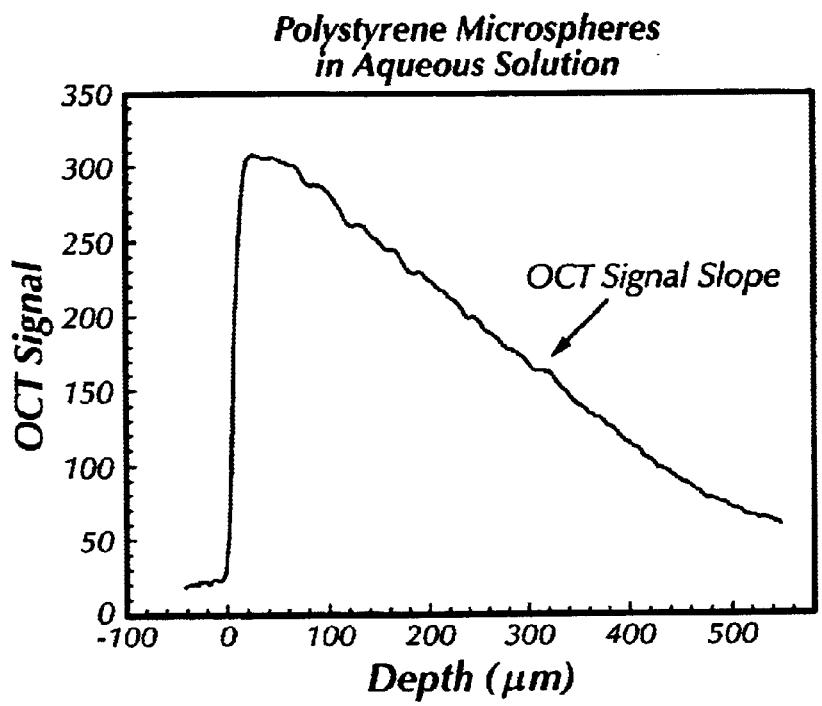
FIG. 1 shows a typical OCT signal obtained from aqueous solution with polystyrene microspheres of diameter 0.76 microns.

The present disclosure addresses many, if not all, of the limitations mentioned above by providing methods and apparatuses that allow for accurate, reliable, noninvasive monitoring of glucose levels within tissue (e.g., within the blood of humans). In specific embodiments described herein, an interferometer that may be low-coherence based, such as an interferometer used for optical coherence tomography (OCT) of tissue, is used to determine glucose concentration with a high degree of accuracy and sensitivity. Due to their high sensitivity and adaptability to monitoring glucose levels within patients having diabetes, the presently-disclosed methods may reduce, or completely eliminate, the need for patients to puncture a finger everyday to determine glucose levels. The low cost and compact dimension of devices using the techniques of this disclosure may result in prevalent home and clinical use. In sum, the present disclosure may greatly improve the way of life for numerous people, while at the same time providing for an effective way to monitor and control the symptoms of diabetes.

Although the applications of the present disclosure are vast, in one embodiment, the disclosed methods and apparatuses may be used as a clinical apparatus and method to monitor the concentration of analytes, including glucose in tissue or body fluid. As used herein, an "analyte" is any substance that is measured. Glucose is an analyte, as are other components of blood or other body fluids. Additionally, the methods described herein may be adapted to one or more software packages that can be used to interpret OCT signals and calculate a concentration of glucose or other analytes using those signals. In other embodiments, the present disclosure may be used as a broad method of treatment, including the monitoring of glucose level of a diabetes patient to treat the diabetes.

Because OCT signals and techniques are discussed herein, a brief background is useful. As will be known to one having ordinary skill in the art, OCT technology may be applied for noninvasive imaging in tissues with high resolution. OCT utilizes sensitive detection of photons coherently scattered from tissue. For imaging and modeling sub-surface physical structures present in tissue and other organs, OCT concerns the use an interferometer, in which light in one arm is aimed into tissue to be imaged. Light that is coherently backscattered from physical structures within the tissue (up to a few millimeters beneath the surface of the tissue) is collected and interfered with light from a reference arm. This interference allows a measurement of the echo time delay and amplitude of the backscattered light. The light shone onto the sample usually has a low coherence. OCT uses correlation to measure the delay, i.e., the depth of the backscattering features. By gathering interference data at points across the surface of a sample, cross-section images can be formed effectively in real time with resolution of 10 microns and even less. Using these types of techniques, researches have demonstrated that they can distinguish normal from abnormal, or precancerous, tissue in the eye, skin, gastrointestinal organs, arteries, and cartilages.

Embodiments described herein take advantage of glucose's ability to decrease tissue scattering. Further, the embodiments described herein also take advantage of glucose's ability to alter optical and morphological characteristics of tissue, body fluids, or implants. Such optical properties include, but are not limited to, scattering, reduced scattering, anisotropic factors, absorption coefficients, indices of refraction, and any other measurable optical characteristic. Such morphological properties include, but are not limited to, properties relating to the form and structure of the tissue, body fluid, or implant, such as, but not limited to, thickness, shape, and any other such measurable feature. It appears that the ability of glucose to decrease tissue scattering is based, at least in part, on its properties as an osmolyte—properties known in the art. Changes in tissue scattering (due to refractive index changes) are more specifically attributed to glucose as an osmolyte than changes in tissue absorption spectra due to the presence of glucose as a chromophore. The scattering coefficient, $\mu_s$, and reduced scattering coefficient, $\mu_s'$, are dependent on the refractive index, n, mismatch between the extracellular fluid and the cellular membranes. In the near infra-red spectral range, the index of refraction of the extracellular fluid (ECF) is 1.348–1.352, whereas the index of refraction of the cellular membranes and protein aggregates is in the range of 1.350–1.460. If the refractive index of the scatterers remains the same and is higher than the refractive index of the extracellular fluid, the increase of glucose concentration in the interstitial space reduces the refractive index mismatch, and, therefore, the scattering coefficient is also reduced.

Therefore, adding glucose to blood will raise the refractive index of the ECF that will decrease the scattering coefficient of the tissue as a whole. Others have observed this effect in tissue-simulating phantoms. For example, this effect has been demonstrated in vivo using a frequency-domain reflectance system on the thigh of a normal volunteer. There, a decrease in $n\mu_s'$ of 2.5% for an increase in blood glucose concentration of 70 mg/dL during glucose tolerance test was observed. Others have used measurements of diffuse reflectance on the skin at distances of 1 to 10 mm from a point source. They demonstrated a correlation between step changes in blood glucose concentration and tissue reduced scattering coefficient in 30 of 41 subject measured. Although the results of these studies are encouraging, detection of diffusively-scattered photons results in low sensitivity and accuracy of glucose concentration measurements due to integration of the signal over the entire optical path in many tissue layers. A blood glucose monitor would need to be more sensitive and accurate than the systems applied in these studies. In other words, known systems and techniques, even if they recognize certain scattering effects of glucose, are not able to provide for the effective, reliable, continuous glucose monitoring made possible by this disclosure.

Embodiments described herein take advantage of the scattering-altering behavior of glucose by using data generated by optical systems that may utilize low-coherence radiation sources to measure glucose concentrations within a specific depth of tissue, body fluid, or an implant within a human. In fact, the methods described herein apply to a vast array of different tissue types including, but not limited to, skin, blood vessels, sclera, lip, tongue, oral tissue, ear, and body fluid such as blood or interstitial fluid. Thus, the methods described herein have wide applicability despite tissue-type differences. Specifically, applying the techniques of the present invention to different tissues will generate successful results, as will be appreciated by those having skill in the art.

Embodiments of this disclosure use a novel optical-based glucose sensor capable of precisely measuring glucose-induced changes in tissue properties such as light scattering from tissue that decreases with the increase of glucose concentration. By measuring the light scattering, which may involve measuring the slope of an OCT signal, and correlating that scattering with glucose levels, glucose concentrations may be monitored noninvasively and continuously. Hence, diabetes itself may be monitored without the need to take a daily blood sample.

Results of the inventors' preliminary studies performed in animals (bolus injections and glucose clamping experiments) demonstrate the capability of this technique to monitor glucose concentration in tissue noninvasively. These, and other studies are discussed below as specific, non-limiting examples.

The following examples are included to demonstrate specific embodiments of the invention. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Animal and Phantom Studies

In this Example, the inventors describe a novel sensor based on optical coherence tomography (OCT) for non-invasive, sensitive, accurate, and continuous monitoring of blood glucose concentration. OCT systems with the wavelength of 1300 nm and 800 nm were used in animal and phantom studies. It will be understood, however, that the light being shone onto a sample may include other wavelengths. Additionally, it will be understood that a single source of radiation may be used or multiple sources may be used. Further, multiple wavelengths may be used in the single-source and multiple-source embodiments.

Polystyrene spheres with the diameter of 0.76 $\mu$m were used as scatterers in aqueous solution in the phantom studies. Bolus glucose injection and glucose clamping experiments were performed in hairless Yucatan micropigs (which are the best model of human skin, as is known in the art), New Zealand rabbits, and dogs.

OCT images were taken constantly from skin (back area of the pigs and rabbit ear), sclera (rabbit), and lip (dog) during these experiments. Blood glucose concentration was monitored with a Beckman glucose analyzer during clamping experiments and with a standard glucose monitoring device ("Lifescan") during bolus glucose injection experiments. Close correlation between blood glucose concentration and slope of the OCT signals was observed. The slope decreased substantially (about 50% in tissues in vivo) and linearly with the increase of blood glucose concentration from 4 to 28.5 mM (which is the physiologic range typical for normal and diabetic subjects).

Figure 6:
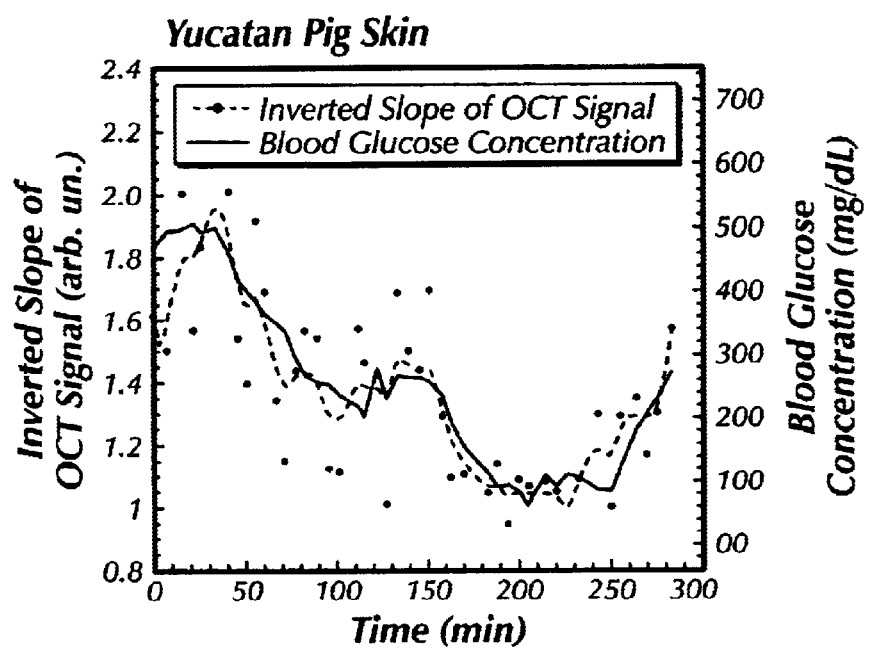
FIG. 6 shows the inverted slope of OCT signals (recorded from Yucatan pig skin) and blood glucose concentration -measured at different times during glucose clamping experiments.
Figure 12:
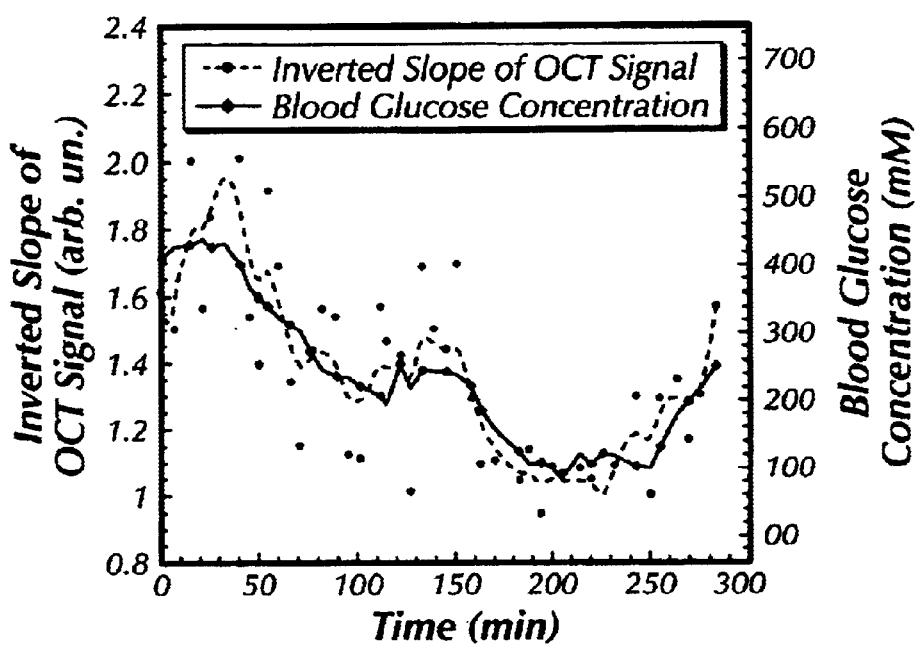
FIG. 12 shows the inverted slope of OCT signals (recorded from Yucatan pig skin) and blood glucose concentration measured at different times during glucose clamping experiments in a different form than is shown in FIG. 6.

Clamping studies confirmed that these changes in the OCT slope were not induced by physiologic response (e.g., blood vessel dilatation, etc.) of the tissues due to the sharp changes in glucose concentration caused by the bolus glucose injections. [Bolus glucose injections are made one at a time, in contrast to glucose clamping, which involves the injection of glucose slowly and continuously in order to maintain glucose at a substantially constant level over a given period of time.] The inverted slope of the OCT signal also followed blood glucose concentration (shown in different forms in FIGS. 6 and 12) during the glucose clamping studies. The inverted slope increased substantially (about 200%) and linearly with the increase of blood glucose concentration from 4 to 28.5 mM (millimols) (the physiologic range typical for normal and diabetic subjects) (shown in different forms in FIGS. 7 and 13). This effect, as described herein, results in high sensitivity and accuracy of glucose concentration measurements with OCT systems.

This Example shows an embodiment using a novel approach for noninvasive glucose monitoring based on measurement and analysis of coherently scattered light from a specific layer of skin with an OCT system. High resolution of this system may allow high sensitivity, accuracy, and specificity of glucose concentration monitoring due to precise measurements of the scattering coefficient from this layer. Coherent detection of the backscattered light may eliminate the influence of changes in optical properties of other tissues.

The aims of this Example were: (1) to evaluate and estimate changes of OCT slope shapes as a function of glucose concentration in tissue phantoms (which may be thought of as controls); and (2) to determine the sensitivity of the OCT system to blood glucose fluctuations in vivo during glucose clamping and bolus injection experiments.

Experimental Setup

Figure 10:
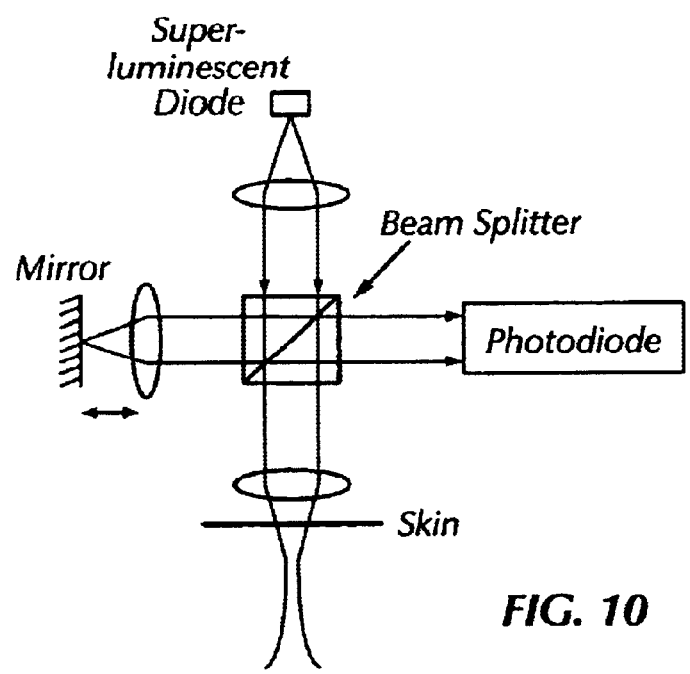
FIG. 10 shows an OCT system suitable for noninvasive glucose monitoring.

Experimental setup for noninvasive glucose monitoring in phantoms and animals is depicted in FIG. 10. Two OCT systems (output power of 0.5 mW—below ANSI standard guidelines for safe light exposure) with wavelengths of 830 and 1300 nm were used in this Example. The OCT system uses an interferometer (see FIG. 10), in which light in one arm is aimed into the objects to be imaged using a quartz beam splitter. Light that is coherently backscattered from structures within the objects (up to 1 mm in depth) is collected and interfered with the light from the reference arm (which is reflected off of, for example, a mirror), allowing a measurement of the echo time delay and amplitude of the backscattered light. The system uses a superluminescent diode—a light source with low coherence—and performs correlation to measure the delay, i.e., the depth of the backscattering features.

By gathering interference data at points across the surface, cross-section images were formed effectively in real time with resolution of about 10 μm. X-Z transverse scanning was about 1 cm. Single transverse scans were accomplished in 3 seconds. Positions of the infrared beams were tracked using a 640 nm CW diode beam, which travels together with the infrared beams. The operation of the OCT scanner was completely automated and controlled by a portable personal computer.

Two types of optical probes were used with OCT systems: X-Z (across the surface and in depth, respectively) scanning probe and X-Z scanning endoscopic optical fiber probe. These probes allow reconstruction of two-dimensional (2-D) images of objects. Two-dimensional intensity distributions from each image were averaged into a single curve to obtain 1-D distribution of light in depth. The 1-D distributions were plotted in logarithmic scale as a function of depth for further analysis. The slopes of obtained OCT signals were calculated and plotted as a function of time during bolus injection and clamping experiments or as a function of blood glucose concentration. Five images were obtained for each data point.

Phantom

Polystyrene microspheres (n=1.57) with the diameter of 0.76 μm were used as scatterers in aqueous solution for the phantoms studies. The phantoms were colored with naphthol green, which has strong absorption in the near infrared spectral range. Six phantoms with the same concentration of polystyrene microspheres and naphthol green and different concentrations of D-glucose (0, 20, 40, 60, 80, and, 100 mM) were utilized in these experiments. The optical properties of the phantoms were chosen to be similar to that of tissue in the NIR spectral range ($\mu_s \cong 100$ cm$^{-1}$, $\mu_a \cong 1$ cm$^{-1}$). The solutions were placed in quartz cuvette with the thickness of 5 mm and the OCT beam was directed perpendicular to the wall of the cuvette.

Animal Studies

Bolus glucose injection and glucose clamping experiments were performed in 2 hairless Yucatan micropigs and 2 New Zealand rabbits. These experiments were also performed in dogs. Animals were pre-anesthetized with standard telazol/xylazine/ketamine mixture given i.m. Full anesthesia was maintained with halothane. Glucose injections were performed through the left femoral vein. OCT images were taken from the dorsal area (micropigs), ear (rabbits), sclera (rabbits), and lip (dog) during these experiments. Blood glucose concentration was monitored with a Beckman glucose analyzer during clamping experiments and with a standard glucometer—"One touch" (Johnson&Johnson)— during bolus injection experiments. Blood samples were taken from the right femoral vein. Euthanasia was performed with saturated potassium chloride i.v.

OCT probes were positioned directly on the surface of the skin with a holder, the design of which is well within the skill level of one of ordinary skill in the art, adapted to avoid motion artifacts. In one embodiment, motion artifacts may be avoided by attaching an OCT probe to the skin (or sample) surface with a double-sided medical adhesive. No adhesive will be in the optical path.

Theoretical Calculations

Mie's theory, known in the art, was applied to predict changes in scattering coefficient, $\mu_s$, and scattering efficiency, $Q_{sca}$, as a function of glucose concentration for the phantoms and tissues. An algorithm known in the art, and given by Bohren and Huffman ("Absorption and Scattering of Light by Small Particles," Wiley, NY, 1983), was applied to polystyrene microspheres (diameter=0.76 μm) and infinite long cylinders (diameter=15 μm) suspended in aqueous media.

The wavelength dependence of refractive index of water, n, is $$n(\lambda) = n_0 + \frac{n_2}{\lambda^2} + \frac{n_4}{\lambda^4} + \frac{n_6}{\lambda^6},$$

(λ in μm). The following fitting parameters were used for water and polystyrene microspheres: $n_0$=1.3199; $n_2$=6.878·10$^3$; $n_4$=−1.132·10$^9$; $n_6$=1.11·10$^{14}$ and $n_0$=1.5626; $n_2$=1.169·10$^4$; $n_4$=−1.125·10$^9$; $n_6$=1.72·10$^{14}$, respectively. The relative change of refractive index as a function of glucose concentration was Δn=2.73·10$^{-5}$ per 1 mM glucose.

Results

After experiments with phantoms and animals, the images were processed and averaged to get 1-D distribution of scatterers in the samples in logarithmic scale. FIG. 1 depicts typical OCT signal obtained from aqueous solution with polystyrene microspheres. Linear fit of the slope of this distribution is proportional to the attenuation coefficient of ballistic photons, $\mu_t = \mu_a + \mu_s$ in the samples, where $\mu_a$ is absorption and $\mu_s$ is scattering coefficients. Since $\mu_a << \mu_s$ in the NIR spectral range, the change in the fit is proportional to change in the scattering coefficient and, therefore, change in the refractive index.

Figure 2:
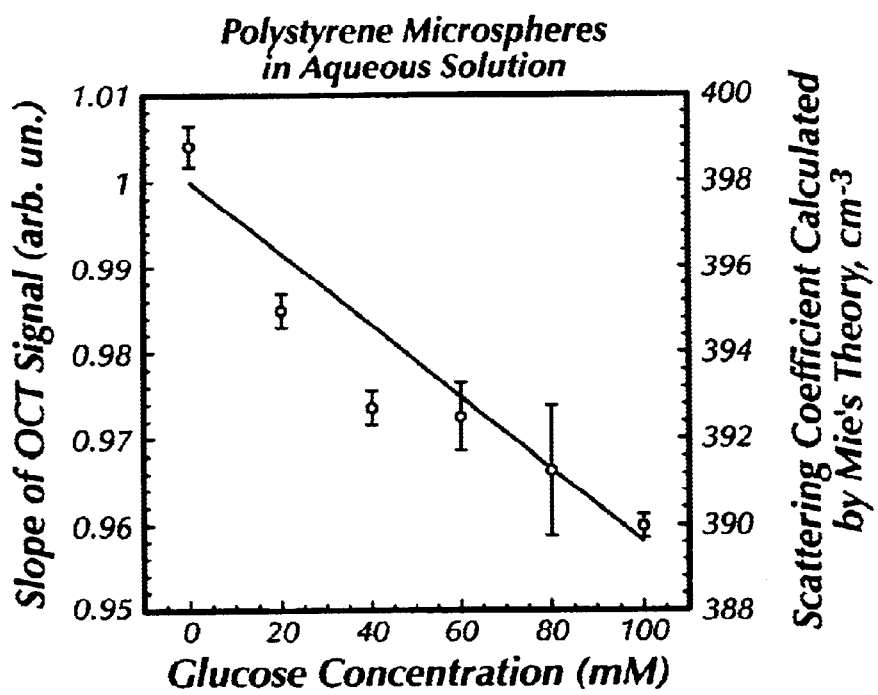
FIG. 2 shows the slope of an OCT signal as a function of glucose concentration in an aqueous solution of polystyrene microspheres. The graph also shows scattering coefficient calculations using Mie's theory.

Five identical experiments were performed with aqueous solutions of polystyrene microspheres. FIG. 2 presents the obtained average slope of OCT signal as a function of glucose. FIG. 2 also shows calculations of scattering coefficient performed using Mie's theory. This figure demonstrates that the decrease of the OCT slope is equal to 4.5% in the range from 0 mM to 100 mM of glucose and is in good agreement with calculations performed with Mie's theory. Error bars show calculated standard deviation of the OCT slope in these experiments.

Figure 3:
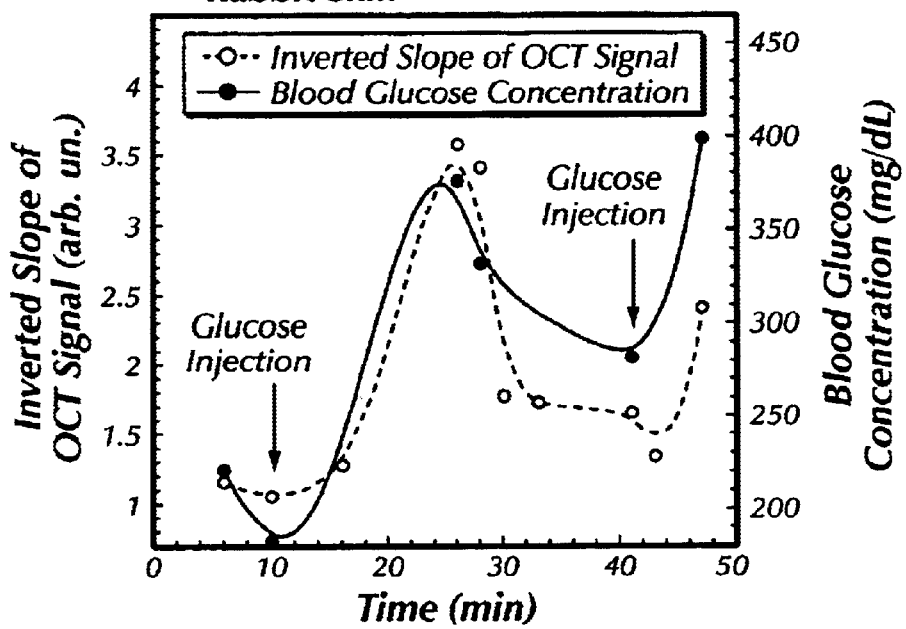
FIG. 3 shows the inverted slope of OCT signals (recorded from rabbit ear) and blood glucose concentration measured at different times during bolus glucose injections.
Figure 4:
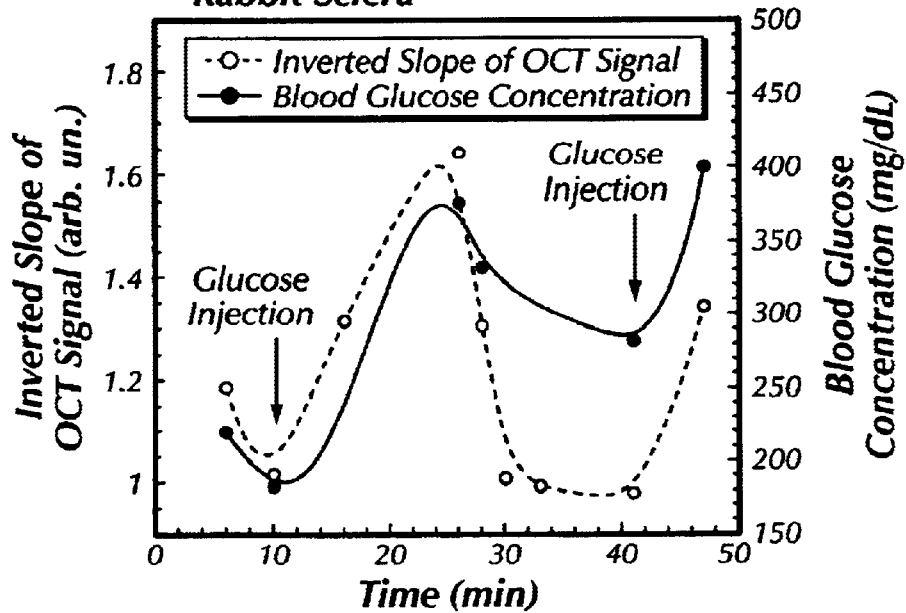
FIG. 4 shows the inverted slope of OCT signals (recorded from rabbit sclera) and blood glucose concentration measured at different times during bolus glucose injections.
Figure 5:
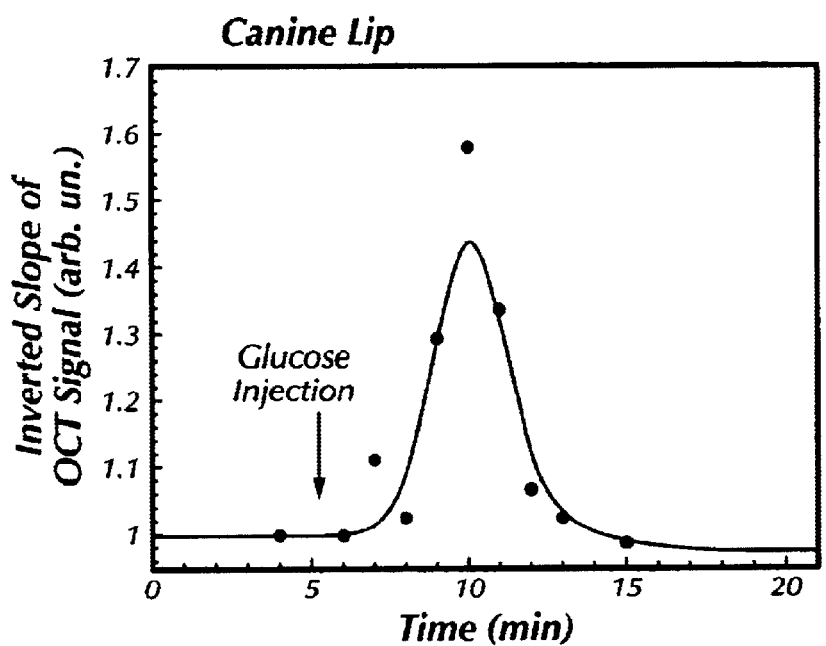
FIG. 5 shows the inverted slope of OCT signals measured at different times during bolus glucose injections from a canine lip.
Figure 11:
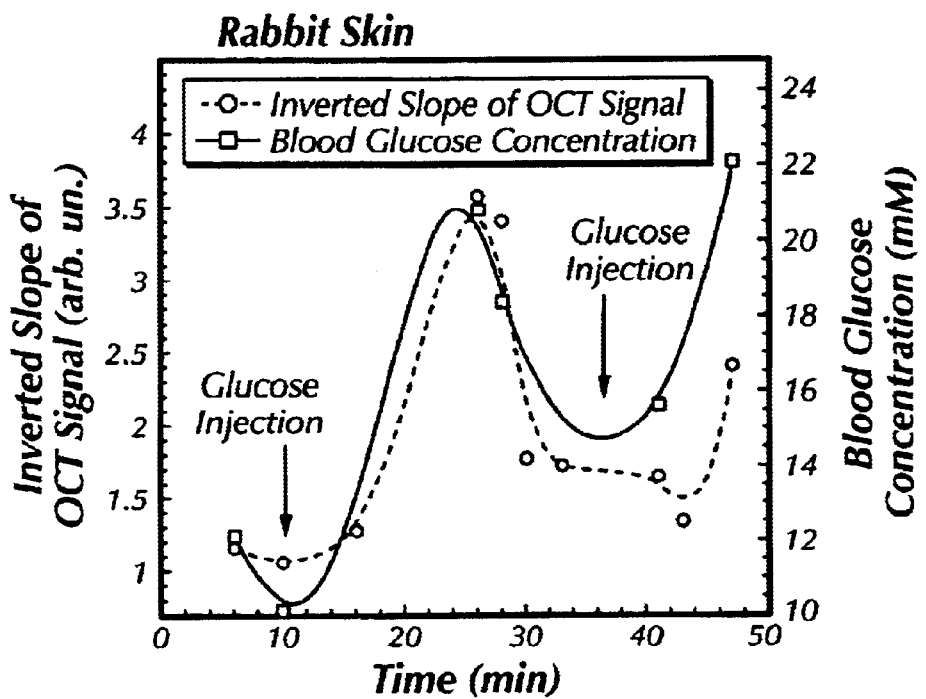
FIG. 11 shows the inverted slope of OCT signals (recorded from rabbit ear) and blood glucose concentration measured at different times during bolus glucose injections in a different form than is shown in FIG. 3.

The changes in the OCT slope recorded in-vivo were substantially greater than the changes obtained in the phantom experiments. The inverted slope of the OCT signal recorded from the rabbit skin and sclera followed blood glucose concentration (as shown in FIG. 3 and FIG. 4) measured at a different time during the bolus injection experiment at a depth of from about 150 μm to about 200 μm. The data recorded from the rabbit skin is presented in a slightly different form in FIG. 11. Good correlation between actual blood glucose concentration and the inverted slope of OCT signal is demonstrated in FIGS. 3 and 11. Similar changes in the OCT signal slope were obtained in the canine lip (shown in FIG. 5).

Bolus glucose injection can induce physiological response of the animals to rapid changes in blood glucose concentrations (changes in cell volume, blood vessel diameter, et al). The inventors performed clamping studies to prove that the changes of OCT slope were not induced by bolus glucose injections. Glucose clamping technique, operated by digitally controlled pump, allows hold at the certain level over long period of time and slow change of the blood glucose concentration. In slightly different forms, FIGS. 6 and 12 demonstrate that the inverted slope of the OCT signal also followed blood glucose concentration during these glucose clamping studies performed on Yucatan micropigs.

Figure 7:
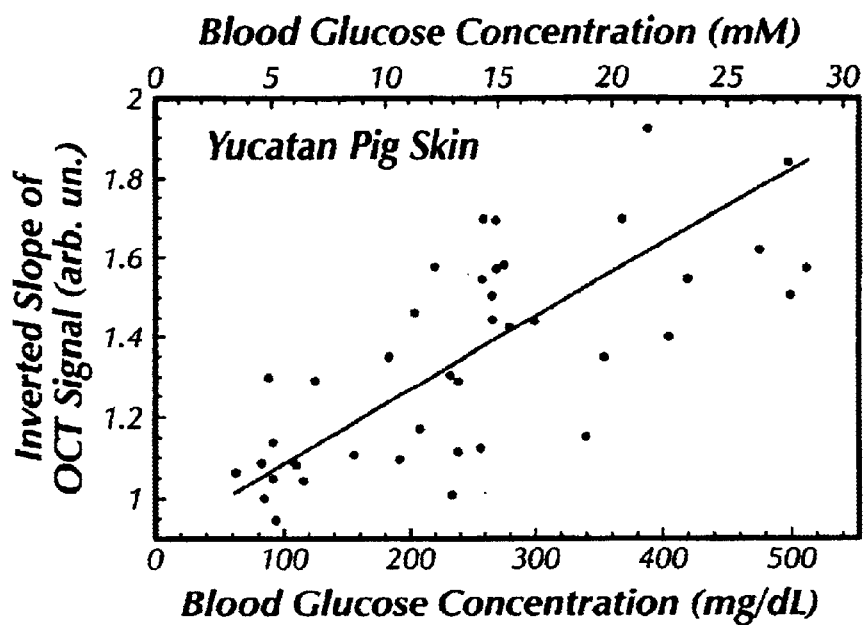
FIG. 7 shows the inverted slope of OCT signals (recorded from Yucatan pig skin) as a function of blood glucose concentration measured during glucose clamping experiments.
Figure 13:
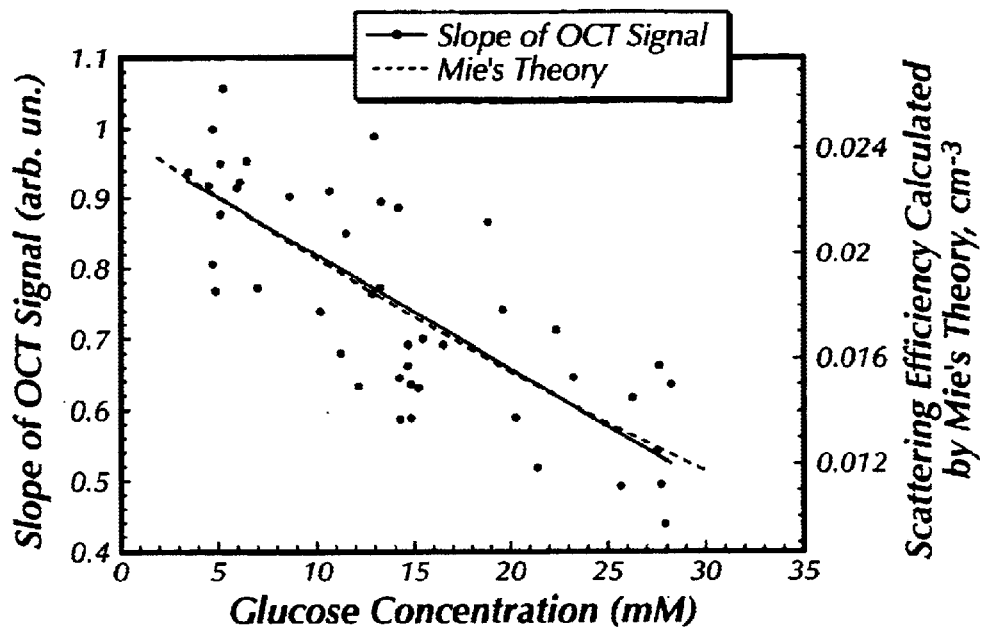
FIG. 13 shows the slope of OCT signals (recorded from Yucatan pig skin) measured during glucose clamping experiments and scattering efficiency as a function of blood glucose concentration in a different form than is shown in FIG. 7.

The slope of OCT system decreases substantially (about 40.5%) and linearly with the increase of blood glucose concentration from 4 to 28.5 mM (physiologic range typical for normal and diabetes subjects) (see FIGS. 7 and 13). Tissue simulating calculations performed on the basis of Mie's scattering on long cylindrical structure reveal good correlation with experiments. Index of refraction of cell membranes was assumed to be 1.360, index of refraction of interstitial fluid −1.357, diameter of scatterers −15 μm.

Discussion

Experiments performed on aqueous solution of polystyrene microspheres reveal linear decrease of OCT signal with the increase of glucose concentration, as shown in FIG. 1. A 4.5% decrease of OCT slope in the range from 0 mM to 100 mM of glucose was obtained. These results were in good agreement with theoretical calculations performed by Mie's theory. Therefore, feasibility of OCT system to detect small changes in scattering coefficient of a turbid (i.e., milky) medium induced by glucose concentration fluctuations has been demonstrated.

The changes in the OCT slope recorded in vivo were substantially greater than the changes obtained in the phantom experiments. For instance, increase in glucose concentration decreased the OCT signal slope by 40.5% in rabbit skin (between maximal and minimal values of blood glucose concentration).

The glucose clamping experiments confirmed that the changes in the OCT slope were not induced by a physiologic response due to the sharp changes in glucose concentration. Results of this study were similar to those obtained during glucose bolus injections. The slope of OCT signal decreases down to 40.5% with the increase of blood glucose concentration from 4 to 28.5 mM (1.65% per 1 mM of glucose).

Mie's light scattering on long dielectric cylinders was applied to predict changes in scattering properties of tissue as a function of glucose concentration (see FIGS. 7 and 13). The exact values of index of refraction of skin component at the depth from 150 to 500 $\mu$m at the wavelength $\lambda$=1300 nm are not known. Values of indexes of refraction of scatterers and interstitial fluid were varied in order to obtain best fit of the experimental data. As a result, relative index of refraction $\Delta n$=0.003 has been obtained. This value seems to be very possible, since indexes of refraction of cell membrane and extracellular fluid can vary from 1.350 to 1.460 and from 1.348 to 1.352, respectively as is known in the art.

Figure 8:
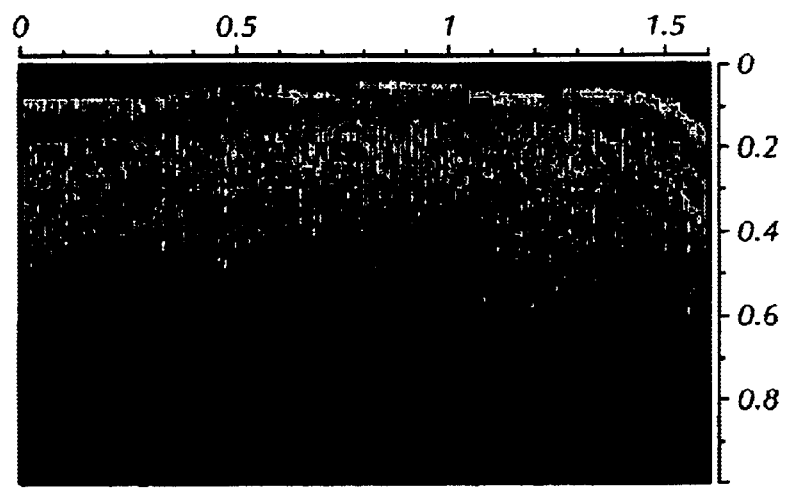
FIG. 8 shows an OCT image of human skin recorded in vivo from a forearm. The scale is in millimeters.
Figure 9:
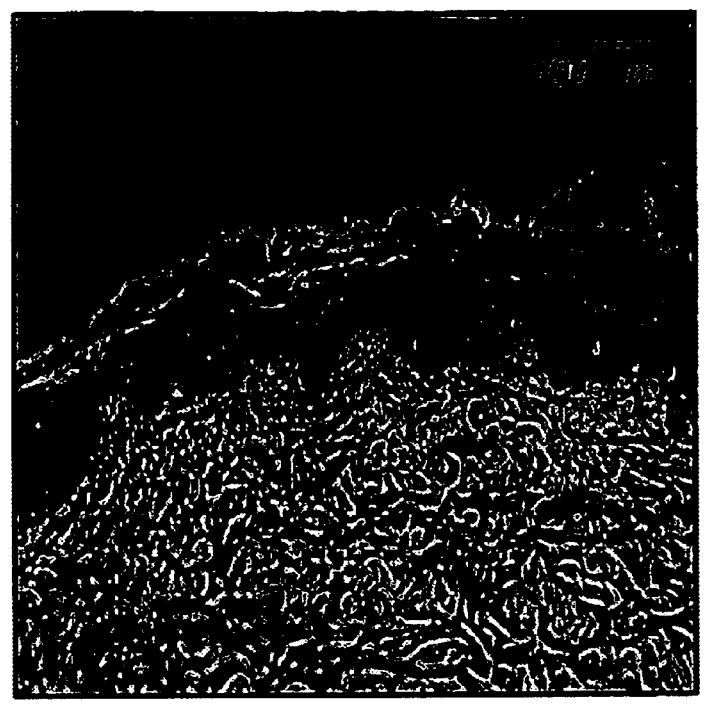
FIG. 9 shows the histology of pig skin (back area).

FIG. 8 and FIG. 9 represent OCT images of the human skin and histology of the Yucatan micropig skin. It is clearly seen that there is a relatively uniform layer at the depth of 150 to 500 $\mu$m in the human and pig skin. The inventors believe that the increase in ECF glucose concentration results in dramatic decrease of scattering in this skin layer because refractive index of ECF is close to the refractive index of tissue components in the layer.

Conclusion

The results of this Example demonstrated: (1) sharp and linear decrease of tissue scattering at depths of about 150 to about 200 $\mu$m, about 150 to about 400 $\mu$m, and about 150 to about 500 $\mu$m measured with the OCT system with the increase of blood glucose concentration and (2) the changes in tissue scattering at these depths are not induced by physiologic response due to bolus glucose injections.

The dependence of OCT slope obtained in our experiments on blood glucose concentration (1.65% per 1 mM of glucose) is substantially greater than was obtained before by other techniques. The inventors believe that this is due to the dependence of scattering coefficient on glucose concentration in the skin layer at the depth of 150 to 500 $\mu$m. The viability of measuring glucose levels in a wide variety of tissues has been demonstrated.

EXAMPLE 2

Uniform Irradiation

To optimize an OCT system for accurate glucose measurement, one may make modifications, within the skill level of one having ordinary skill in the art, to ensure accurate measurement of scattering at depths ranging between about 150 $\mu$m and about 500 $\mu$m. More particularly, modifications may be made to ensure accurate measurements at depths ranging between about 150 $\mu$m and about 400 $\mu$m, and/or between about 150 $\mu$m and about 200 $\mu$m. Modifications may involve (see FIG. 10) choosing a lens that can provide uniform irradiation of skin at this depth. Such a modification is within the skill level of one having ordinary skill in the art.

The choosing of the lens may allow precise measurement of OCT slope at these depth ranges and, therefore, glucose concentration in a wide variety of samples and tissues, including dermal ISF. As will be apparent to those having skill in the art with the benefit of this disclosure, experiments involving no undue experimentation may be performed in turbid phantoms (aqueous solutions and gels with polystyrene spheres and naphthol green) with well-defined optical properties similar to that of human skin. Influence of temperature on the accuracy of OCT slope measurements may be evaluated in these phantoms too. Temperature changes may be about 5° C. that are typical to temperature variation in human skin in-vivo.

EXAMPLE 3

Changes in OCT Slope With Refractive Index

Using the techniques described herein, one may study the mechanism of sharp changes in OCT slope with changes in refractive index of various samples and tissue, including ISF. Experiments may be performed with hairless Yucatan micropigs (e.g., 5 animals). Dextrane (M.W.=50,000) may be injected intravenously to substantially increase the refractive index of ISF. Since dextrane molecules will not penetrate into skin cells, the scattering coefficient may decrease sharply. Dextrane concentration may be varied from about 0 to about 50 mM.

OCT data may be taken from the back area. Dermal ISF may be collected with thin needles and dextrane concentration may be measured with HPLC. Correlation between OCT signal slope and dextrane concentration may then be assessed. Conclusions may then be made on the mechanism of the sharp changes in OCT slope with changes in refractive index of ISF. These conclusions may then be applied to other tissue and sample types, and these conclusions may then be used to measure glucose concentrations as will be apparent to those having skill in the art with the benefit of this disclosure.

EXAMPLE 4

Testing System Performance

Using the techniques described herein, one may test system performance in animal studies. For example, hairless Yucatan micropigs (e.g., 15 animals) may be used in these studies. Glucose clamps may be maintained at 3, 7, 10, 15, 20, 25, and 30 mM, and OCT data acquisition may be performed simultaneously with blood glucose measurements. The accuracy and sensitivity of OCT glucose concentration measurements may then be evaluated.

EXAMPLE 5

Clinical Trials

Using the techniques described herein, one may conduct clinical trials with an OCT system to measure glucose concentration in humans. The system may be evaluated in normal and diabetic subjects. Oral glucose tolerance test may be performed in, for example, 20 volunteers (e.g., 10 normal and 10 diabetic subjects). Glucose clamping studies may be conducted in, for example, 10 volunteers (e.g., 5 normal and 5 diabetic subjects).

EXAMPLE 6

Polarization

One may compare glucose monitoring in normal and orthogonal polarization using the techniques described herein. OCT images in orthogonal polarization may potentially provide higher sensitivity and specificity of glucose monitoring.

Experiments may be performed with, for example, 12 hairless Yucatan micropigs. Six animals may be used for the experiment with normal and 6 animals for the experiment with orthogonal polarization. Glucose clamps may be maintained, for example, at 3, 15, and 30 mM. OCT images may be taken from the dorsal area. Glucose concentration may be measured with a Beckman glucose analyzer.

Conclusions may be made on the sensitivity and accuracy of glucose concentration monitoring in normal or orthogonal polarization. The best regime of OCT image acquisition (normal or orthogonal polarization) may then be chosen and used in further monitoring situations.

An OCT unit may be used, as is known in the art, to record tomograms on an orthogonal polarization channel (with respect to the incident polarization). Contributions to the interferometric signal are produced by those regions within the tissue that depolarize the light upon backscattering. To receive a signal from the tissue in the orthogonal polarization, a Faraday rotator may be mounted in the reference arm. Backscattered light that changes polarization can be interferometrically sensed by the photodetector.

OCT imaging with an orthogonal polarization may provide higher sensitivity and specificity of glucose monitoring, because (1) skin reflects light in the orthogonal polarization and (2) glucose solutions rotate polarization. These two effects may contribute to the OCT signals recorded in the orthogonal polarization and, therefore, can be used for more accurate glucose sensing.

Experiments may be performed, for example, with 12 hairless Yucatan micropigs (weight ~15 kg). Six animals may be used for the experiment without the Faraday rotator and 6 for the experiment with it. Pigs may be pre-anesthetized with standard telazol/xylazine/ketamine mixture given i.m. Full anesthesia may be maintained with halothane. Glucose clamps may be maintained at 3, 15, and 30 mM. Glucose and insulin injections may be performed through the left femoral vein and ear vein, respectively. OCT images may be taken from the dorsal area. Glucose concentration may be measured with a Beckman glucose analyzer. Blood samples may be taken from the right femoral vein. Euthanasia will be performed with saturated potassium chloride i.v.

Correlation between OCT signal slope and blood glucose concentration may then be assessed for the experiments with and without the Faraday rotator. Conclusions may be made on the sensitivity and accuracy of glucose concentration monitoring with and without the Faraday rotator. The best regime of OCT image acquisition (normal or orthogonal polarization) may then be chosen and used in further monitoring situations.

EXAMPLE 7

Data

Figure 14:
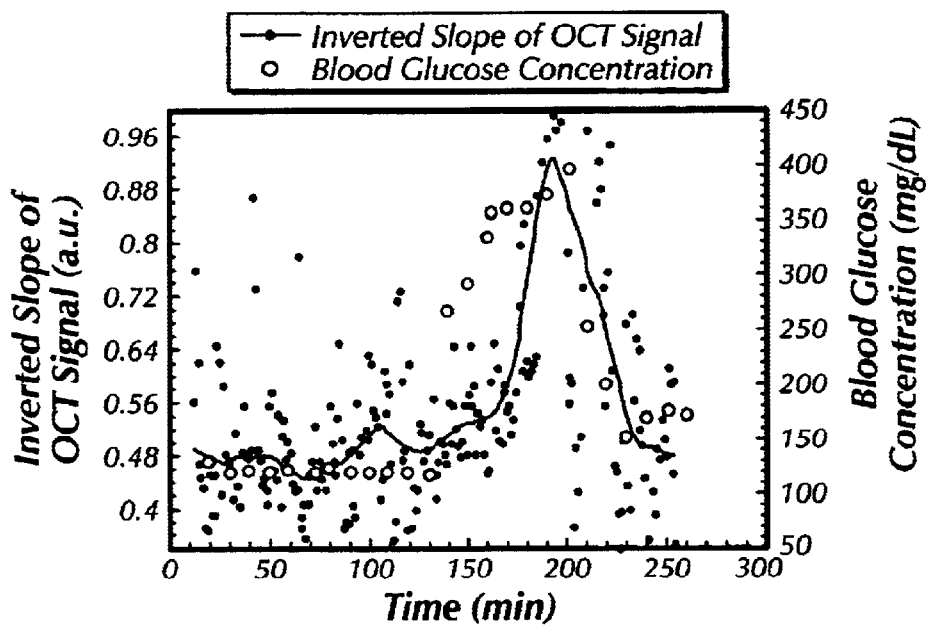
FIG. 14 shows the inverted slope of OCT signals as a function of blood glucose concentration (1 mM=18 mg/dL) for Yucatan pig skin. Measurements were performed in vivo during glucose clamp. The wavelength was 1300 nm.
Figure 15:
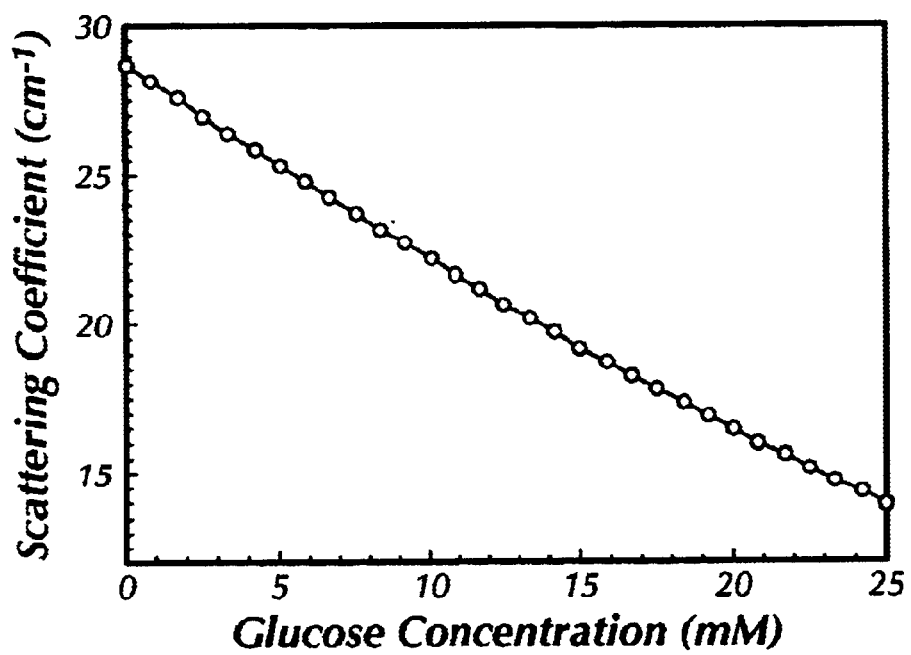
FIG. 15 shows theoretical calculations of scattering coefficients of spherical cells in an extracellular medium as a function of glucose concentration. The calculations were performed using Mie scattering theory.

FIG. 14 and FIG. 15 show further data taken in accordance with the present disclosure. FIG. 14 is a graph of inverted slope of an OCT signal as a function of blood glucose concentration (1 mM=18 mg/dL) for Yucatan pig skin. Measurements were performed in vivo during glucose clamp. The wavelength was 1300 nm.

FIG. 15 shows theoretical calculations of scattering coefficient of spherical cells in extracellular medium as a function of glucose concentration. Calculations were performed by using Mie scattering theory with the following parameters: cell diameter=15 microns, refractive index=1.36, $\Delta n$=0.03, and wavelength=1300 nm.

EXAMPLE 8

Software

With the benefit of the present disclosure, it will be apparent to those having skill in the art that calculating glucose concentrations within tissue may be assisted with software configured to analyze an OCT signal and calculate glucose concentration using, that signal. Programming software suitable to perform that task is well within the skill level of one of ordinary skill in the art.

In one embodiment, software may do the following: (a) gather signals from an OCT apparatus, (b) store those signals in memory, (c) perform data analysis on those signals to determine an OCT signal slope, or inverted slope, (d) correlate the slope, or inverted slope, with a glucose concentration, and (e) display the calculated glucose concentration to a user through, for example, a graphical user interface such as a computer screen.

Portions of such software may include commercially-available software tools. For instance, a software package such as LabView (National Instruments) may be used for the task of gathering and storing OCT signals. To perform the data analysis and correlation of slope to glucose concentration, one may perform the calculations and methodology as described herein by using any number of programming languages. For instance, a stand-alone program written in, for instance, C++, visual basic, FORTRAN, or the like may be used. Alternatively, a specialized script, configured to perform glucose calculations, may be written for use with another commercially-available data analysis software package. To display the glucose concentration, any software tool or program may be used, as will be apparent to those having skill in the art.

This software may be integrated into a computer, into an OCT system, into a hand-held device, or the like, depending on the application. For instance, in a lab setting, the software may be hosted on a lab computer workstation. In a home setting, the software may be resident on a home computer or on a hand-held device. Alternatively, the software may run within the OCT system itself so that a single unit could be used for the testing of tissue as well as the display of glucose concentration.

EXAMPLE 9

Implantable Probes

As described herein, analyte concentrations of tissue may be determined by analyzing, through OCT, optical and/or morphological changes (changes induced by the analyte) in the tissue. As will be apparent to those having skill in the art with the benefit of the present disclosure, one or more probes may be used to enhance such optical and/or morphological characteristics. As used herein, a probe means any biocompatible material that may be injected into tissue.

In particular, a probe may be implanted into tissue that will generate a change in, for instance, scattering above and beyond the change that would be induced by the analyte alone. Implantation may be done through injection, surgical procedure, or any other method known in the art. The enhanced change in tissue characteristics, of course, alters the OCT signal. This enhanced change may be more easily measured with the OCT system, and the sensitivity of the process (and of the OCT signal) may be correspondingly improved. As with other examples described herein, the change in tissue property (this time, enhanced by a probe) may then be correlated with an analyte concentration, such as glucose concentration.

Specifically, the use of a polymer-based probe may improve the signal-to-noise ratio and, thus, allow for a more accurate and potentially less expensive method of noninvasively monitoring analytes such as glucose. A biocompatible, polymer-based probe, or sensor, may be implanted in skin or other sites, such as the oral cavity, where changes in optical and/or morphological properties of the probe as function of analyte concentration may be monitored using OCT accomplished through, for example, a low-coherence interferometer. Changes to the probe's optical and/or morphological properties may facilitate the direct correlation of the change in optical path length to the concentration of an analyte such as glucose. The probe may be designed to function as a multi-layered optical element with reflective surfaces and optical properties that will change as a function of the concentration of the analyte under consideration.

All of the methods and apparatuses disclosed and claimed herein can be made and executed without undue experimentation in light of the present disclosure. While the techniques of this invention have been described in terms of specific embodiments, it will be apparent to those of skill in the art that variations may be applied to the disclosed methodologies and in the steps of the method described herein without departing from the concept, spirit, and scope of the invention.

REFERENCES

The following references are specifically incorporated herein by reference.

1. National institute of Diabetes and Digestive and Kidney Diseases. "Diabetes Overview", NIH, 94–3235, (1994).
2. Cote G. L., Fox M. D., and Northrop R. B., "Noninvasive optical polarimetric glucose sensing using a true phase measurement technique", IEEE Transactions on Biomedical Engineering, 39(7). 752–756. (1992).
3. King T. W., Cote G. L., McNichols R., and Goetz Jr. M. J., "Multispectral polarimetric glucose detection using a single Pockels cell", Optical Engineering, 33(8). 2746–2753, (1994).
4. Goetz Jr. M-L, Cote G. L., March W. E., Erckens R., and Motamedi M., "Application of a multivariate technique to Raman spectra for quantification of body chemicals", IEEE Transactions on Biomedical Engineering, 42(7), 728–731, (1995).
5. Wicksted J. P., Erkens R. J., Motamedi M., and March W. E., "Monitoring of aqueous humor metabolites using Raman spectroscopy", SPIE Proceedings, 2135. 264–274, (1994).
6. Pan S., Chung H., Arnold M. A., and Small G. W., "Near-infrared spectroscopic measurement of physiological glucose levels in variable matrices of protein and triglycerides", Anal. Chem., 68, 1124–1135, (1996).
7. Robinson M. R., Eaton R. P., Haaland D. M., Koepp G. W., Thomas E. V., Stallard B. R., and Robinson P. L., "Noninvasive glucose monitoring in diabetic patients: A preliminary evaluation", Clin. Chem., 38(9), 1618–1622, (1992).
8. Kohl M., and Cope M., "Influence of glucose concentration on light scattering in tissue-simulating phantoms", Optics letters, 19(24). 2170–2172, (1994).
9. Maier J. S., Walker S. A., Fantini S., Fmnceschini M. A., and Gratton E., "Possible correlation between blood glucose concentration and the reduced scattering coefficient of tissue in the near infrared", Optics Letters, 19(24), 2062–2064, (1994).
10. Cote G. L., "Noninvasive optical glucose sensing—an overview", Journal of Clinical Engineering, 22(4), 253–259, (1997).
11. Tuchin V. V., Maksimova L, Zimnyakov D., et.al., "Light propagation in tissues with controlled optical properties", Proc. SPIE, 2925. 118–142, (1996).
12. Fercher A F, Hitzenberger C K, Drexler W, Kamp G, Sattmann H., "In vivo Optical Coherence Tomography", Amer. Journ. of Ophthalm. 116, No. 1, 113–114 (1993).
13. Sergeev A M, Gelikonov M, Gelikonov G V, Feldchtein F I, Pravdenko K I, D.Shabanov D V, Gladkova N D, Pochinko V V, Zhegalov V A, Dmitriev G I, Vazina I R, Petrova G A, Nikulin N K, "In vivo optical coherence tomography of human skin microstructure", Proc. SPIE 2328, 144–150 (1994).
16. Fuji i M, Yamanouchi S, Hori N, Iwanaga N, Kawaguchi N, Matsumoto M., "Evaluation of Yucatan Micropig Skin for Use as an in Vitro Model for Skin Permeation Study", Biol. Pharm. Bull. 20 (3): 249–254, (1997).
19. Bohren C. F. and Huffman D. R., "Absorption and Scattering of Light by Small Particles", Wiley, NY, (1983).
20. Bantle J P, Thomas W., "Glucose measurement in patients with diabetes mellitus with dermal interstitial fluid", J Lab Clin Med, 130 (4): 436–441, (1997).
21. Service E J, O'Brien P C, Wise S D, Ness S, LeBlanc S M, "Dermal Interstitial Glucose as an Indicator of Ambient Glycernia", Diabetes Care, 20 (9): 1426–1429, (1997).
22. American Diabetes Association. "Economic consequences of diabetes mellitus in the U.S. in 1997", Diabetes Care, 21(2), 296–309, 1998.
23. Larin K. V., Oraevsky A. A., "Optoacoustic signal profiles for monitoring glucose concentration in turbid media", Proc. SPIE, 3726,576–583, 1998.
24. Lentmer C., ed., "Geigy Scientific Tables", 3, 69, 1984.
25. Weast R. C., ed., "CRC Handbook of Chemistry and Physics", 70th ed., CRC, Cleveland, Ohio, 1989.
26. Duck F. A., "Physical Properties of Tissue", Academic, London, 1990.
27. Bruulsema J. T., Hayward J. E., Farrell T. J., Patterson M. S., Heinemann L., Berger M., Koschinsky T., Sandahl-Christansen J., Orskov H., Essenpries M., Schmelzeisen-Redeker G., Bocker D., "Correlation between blood glucose concentration in diabetics and noninvasively measured tissue optical scattering coefficient", Optics Letters, 22(3), 190–193, 1997.
28. Huang D., Swanson E. A., Lin C. P., Schuman J. S., Stinson W. G., Chang W., Hee M. R., Flotte T., Gregory 28. K., Puliafito C. A., and Fujimoto J. G., "Optical coherence tomography", Science, 254, 1178–1181, 1991.
29. Gladkova N. D., Petrova G. A., Nikulin N. K., Gelikonov G. V., Gelikonov V. M., and Feldchtein F. I., "Optical coherence tomography as a technique for diagnostics of skin changes at rheumatic diseases", EULAR Journal, 24, 256–256, 1995.
30. Roper S. N., Moores M. D., Gelikonov G. V., Feldchtein F. I., Beach N. M., King M. A., Gelikonov V. M., Sergeev A. M., and Reitze D. H., "In vivo detection of experimentally induced cortical dysgenesis in the adult rat using optical coherence tomography", J. Neurosci. Meth., 80, 91–98, 1998.
31. Teamey G. J., Brezinski M. E., Bouma B. E., Boppart S. A., Pitris C., Southern J. F., and Fujimoto J. G., "In vivo endoscopic optical biopsy with optical coherence tomography", Science, 276,2037–2039, 1997.
32. Sergeev A. M., Gelikonov V. M., Gelikonov G. V., Feldchtein F. I., Kuranov R. V., Gladkova N. D., Shakhova, L. B. Snopova, A. V. Shakhov, I. A. Kuznetzova, A. N. Denisenko, V. V. Pochinko, Yu. P. Chumakov N. M., and Strelzova O. S., "In vivo endoscopic OCT imaging of precancer and cancer states of human mucosa," Opt. Exp., 1, 432–439, 1997.
33. Boppart S. A., Tearney G. J., Bouma B. E., Southern J. F., Brezinski M. E., and Fujimoto J. G., "Noninvasive assessment of the developing Xenopus cardiovascular system using optical coherence tomography", Proc. Natl. Acad. Sci., 94, 4256–4261, 1997.
34. Brezinski M. E., Tearney G. J., Weissman N. J., Boppart S. A., Bouma B. E., Hee M. R., Weyman A. E., Swanson E. A., Southern J. F., and Fujimoto J. G., "Assessing atherosclerotic plaque morphology: comparison of optical coherence tomography and high frequency intravascular ultrasound", Heart, 77, 397–403, 1997.
35. Brezinski M. E., Tearney G. J., Boppart S. A., Swanson E. A., Southern J. F., and Fujimoto J. G., "Optical biopsy with optical coherence tomography: feasibility for surgical diagnostics", J. Surg. Res., 71, 32–40, 1997.
36. Izatt J. A., Kulkarni M. D., Yazdanfar S., Barton J. K., and Welch A. J., "In vivo bidirectional color Doppler flow imaging of picoliter blood volumes using optical coherence tomography", Op. Lett., 22, 1439–1442, 1997.
37. Chen Z., Milner T. E., Srinivas S., Wang X., Malekafzali A., van Gemert M. J. C., and Nelson J. S., "Noninvasive imaging of in vivo blood flow velocity using optical Doppler tomography," Op. Lett., 22, 1119–1121, 1997.
38. Colston B. W., Everett M. J., Da Silva L. B., Otis L. L., and Nathel H., "Optical coherence tomography for diagnosing periodontal disease", Proc. SPIE, 2973, 216–220, 1997.
39. Colston B. W.; Everett M. J., Da Silva L. B., Otis L. L., Stroeve P., and Nathel H., "Imaging of hard- and soft-tissue structure in the oral cavity by optical coherence tomography", Appl. Opt., 37, 3582–3585, 1998.
40. Warren Jr. J. A., Gelikonov G. V., Gelikonov V. M., Feldchtein F. I., Sergeev A. M., Beach N. M., Moores M. D., and Reitze D. H., "Imaging and characterization of dental structure using optical coherence tomography", Optical Society of America Technical Digest Series, 6, 128, 1998.
41. Kurihara-Berhstrom T, Woodworth M, Feisullin S, Beall P., "Characterization of the Yucatan Miniature Pig Skin and Small Intestine for Pharmaceutical Applications", Laboratory Animal Science, 36(4), 396–399, 1986.
42. Van de Hulst H. C., "Light Scattering by Small Particles", Dover Publications, Inc., NY, 1981.
43. Kohl M., Essenpreis M., Cope M., "The influence of glucose concentration upon the transport of light in tissue-simulating phantoms", Phys.Med.Biol, 40, 1267–1287, 1995.

What is claimed is:

1. A method for measuring glucose concentration within a tissue, comprising:

generating radiation;

directing a first portion of the radiation to the tissue to generate backscattered radiation;

directing a second portion of the radiation to a reflector to generate reference radiation;

detecting the backscattered radiation and the reference radiation to produce an optical coherence tomography signal; and calculating the glucose concentration using a slope of the optical coherence tomography signal.

2. The method of claim 1, wherein generating radiation comprises generating low-coherence radiation.

3. The method of claim 2, wherein generating low-coherence radiation comprises generating low-coherence radiation using a super-luminescent diode.

4. The method of claim 1, wherein generating radiation comprises generating radiation from a plurality of sources.

5. The method of claim 4, wherein two or more of the sources emit radiation having different wavelengths.

6. The method of claim 1, wherein a wavelength of the backscattered radiation is substantially equal to a wavelength of the reference radiation.

7. The method of claim 1, wherein the radiation has a first polarization and the backscattered radiation has a second polarization, the second polarization being different from the first polarization.

8. The method of claim 1, wherein the tissue comprises skin.

9. The method of claim 1, wherein the tissue comprises a blood vessel.

10. The method of claim 1, wherein the tissue comprises sclera.

11. The method of claim 1, wherein the tissue comprises lip.

12. The method of claim 1, wherein the tissue comprises tongue.

13. The method of claim 1, wherein the tissue comprises oral tissue.

14. The method of claim 1, wherein the tissue comprises ear.

15. The method of claim 1, wherein the backscattered radiation emanates from a tissue depth of between about 150 $\mu$m and about 500 $\mu$m.

16. The method of claim 1, wherein the backscattered radiation emanates from a tissue depth of between about 150 $\mu$m and about 400 $\mu$m.

17. The method of claim 1, wherein the backscattered radiation emanates from a tissue depth of between about 150 $\mu$m and about 200 $\mu$m.

18. The method of claim 1, wherein directing the first portion of the radiation comprises scanning the first portion of the radiation across a specified portion of the tissue.

19. The method of claim 1, wherein the calculating comprises determining a glucose-induced change in an optical property of the tissue.

20. The method of claim 19, wherein the optical property comprises scattering, anisotropic factors, absorption, or index of refraction.

21. The method of claim 1, wherein the calculating comprises determining a glucose-induced change in morphology of the tissue.

22. The method of claim 21, wherein the morphology comprises thickness or shape.

23. A method for measuring glucose concentration within a tissue, comprising:

detecting radiation backscattered from the tissue and reference radiation to generate an optical coherence tomography (OCT) signal; and determining the glucose concentration within the tissue using a slope of the OCT signal.

24. The method of claim 23, wherein a wavelength of the radiation backscattered from the tissue is substantially equal to a wavelength of the reference radiation.

25. The method of claim 23, wherein the tissue comprises skin.

26. The method of claim 23, wherein the tissue comprises a blood vessel.

27. The method of claim 23, wherein the tissue comprises sclera.

28. The method of claim 23, wherein the tissue comprises lip.

29. The method of claim 23, wherein the tissue comprises tongue.

30. The method of claim 23, wherein the tissue comprises oral tissue.

31. The method of claim 23, wherein the tissue comprises ear.

32. The method of claim 23, wherein the radiation backscattered from the tissue emanates from a tissue depth of between about 150 $\mu$m and about 500 $\mu$m.

33. The method of claim 23, wherein the radiation backscattered from the tissue emanates from a tissue depth of between about 150 $\mu$m and about 400 $\mu$m.

34. The method of claim 23, wherein the radiation backscattered from the tissue emanates from a tissue depth of between about 150 $\mu$m and about 200 $\mu$m.

35. The method of claim 23, wherein using the slope comprises correlating the slope with an optical property of the tissue.

36. The method of claim 23, wherein using the slope comprises correlating the slope with a morphological property of the tissue.

37. The method of claim 23, wherein using the slope comprises correlating a percentage change in the slope with a change in glucose concentration.

38. A method for measuring analyte concentration within a tissue, comprising:

implanting a probe within the tissue, the probe configured to alter an optical coherence tomography (OCT) signal of the tissue;

generating an OCT signal of the tissue, the OCT signal being altered by the probe; and correlating a change in slope of the OCT signal with the analyte concentration within the tissue.

39. The method of claim 38, wherein the analyte concentration comprises glucose concentration.

40. The method of claim 38, wherein the probe is configured to increase a sensitivity of the OCT signal.

41. The method of claim 38, wherein the tissue comprises skin.

42. A computer readable media containing program instructions for measuring glucose concentration within a tissue, the computer readable media comprising:

instructions for storing an optical coherence tomography (OCT) signal in memory; and instructions for determining the glucose concentration within the tissue using the signal, wherein the instructions for determining the glucose concentration comprise:

determining a slope of the OCT signal; and determining the glucose concentration using the slope.

43. A computer readable media containing program instructions for measuring glucose concentration within a tissue, the computer readable media comprising:

instructions for storing an optical coherence tomography (OCT) signal in memory; and instructions for determining the glucose concentration within the tissue using the signal, wherein the instructions for determining the glucose concentration comprise: instructions for correlating a change in the slope with an optical or morphological change in the tissue.

44. A method for measuring glucose concentration within a tissue, comprising:

generating radiation;

directing a first portion of the radiation to the tissue to generate backscattered radiation;

directing a second portion of the radiation to a reflector to generate reference radiation;

detecting the backscattered radiation and the reference radiation across a surface and in a depth to produce a two-dimensional image;

processing the two-dimensional image into a one-dimensional signal; and calculating the glucose concentration using a slope of the one-dimensional signal.

* * * * *

UNITED STATES PATENT AND TRADEMARK OFFICE
CERTIFICATE OF CORRECTION

PATENT NO. : 6,725,073 B1
DATED : April 20, 2004
INVENTOR(S) : Motamedi et al.

It is certified that error appears in the above-identified patent and that said Letters Patent is hereby corrected as shown below:

Column 18,
Lines 16, 18, 37, 63 and 64, delete "the radiation" and insert -- the generated radiation --.

Column 20,
Line 34, delete "comprise:" and insert -- comprise --, delete "the slope" and insert -- slope of the OTC signal --.
Line 40 and 42, delete "the radiation" and insert -- the generated radiation --.

Signed and Sealed this

Twenty-eighth Day of September, 2004

JON W. DUDAS
*Director of the United States Patent and Trademark Office*